(12) United States Patent
Calanchi et al.

(10) Patent No.: US 6,509,034 B1
(45) Date of Patent: Jan. 21, 2003

(54) WETTABLE MICROCAPSULES HAVING HYDROPHOBIC POLYMER COATED CORES

(75) Inventors: Massimo Maria Calanchi, Sesto s. Giovanni (IT); Stefano De Luigi Bruschi, Milan (IT); Leonardo Gentilini, Milan (IT); Luigi Giovanni Mapelli, Milan (IT)

(73) Assignee: Eurand International S.p.A. (IT)

( * ) Notice: Subject to any disclaimer, the term of this patent is extended or adjusted under 35 U.S.C. 154(b) by 0 days.

(21) Appl. No.: 09/673,178

(22) PCT Filed: Apr. 9, 1999

(86) PCT No.: PCT/EP99/02430

§ 371 (c)(1),
(2), (4) Date: Oct. 10, 2000

(87) PCT Pub. No.: WO99/52510

PCT Pub. Date: Oct. 21, 1999

(30) Foreign Application Priority Data

Apr. 9, 1998 (EP) ............................................. 98106521

(51) Int. Cl.[7] .................................................. A61K 9/50
(52) U.S. Cl. ....................... 424/451; 424/489; 424/490; 424/495; 424/452
(58) Field of Search ................................ 424/490, 495, 424/489, 452, 451

(56) References Cited

U.S. PATENT DOCUMENTS

| 3,415,758 | A |   | 12/1968 | Powell et al. ................. 252/316 |
| 3,748,277 | A |   | 7/1973 | Wagner ....................... 252/316 |
| 4,259,315 | A |   | 3/1981 | Lippmann et al. ............. 424/37 |
| 5,158,779 | A | * | 10/1992 | Gergely et al. ............. 424/490 |
| 5,192,522 | A | * | 3/1993 | Fekete et al. ............... 424/4.95 |
| 5,972,383 | A | * | 10/1999 | Gibson ........................ 424/489 |
| 6,022,562 | A | * | 2/2000 | Autant et al. ................ 424/489 |

* cited by examiner

*Primary Examiner*—Thurman K. Page
*Assistant Examiner*—Rachel M. Bennett
(74) *Attorney, Agent, or Firm*—Thompson Hine LLP

(57) ABSTRACT

This invention concerns wettable microcapsules ethylcellulose coated cores and to processes for their preparation; in particular, to microcapsules with ethylcellulose coats that are wettable so that they are suspendable in aqueous medium. The wettable microcapsules can be prepared by applying ethylcellulose onto drug containing core by phase separation from a solvent to provide microcapsules, optionally washing said microcapsules with a solvent in which said microcapsules are substantially insoluble and drying, (a) one or more surfactants is/are incorporated in the solvent at the phase separation step; and/or (b) one or more surfactants is/are incorporated in the solvent used to wash the microcapsules; and/or said microcapsules being coated with one or more surfactants optionally in the presence of a binder.

8 Claims, No Drawings

WETTABLE MICROCAPSULES HAVING HYDROPHOBIC POLYMER COATED CORES

The present invention relates to wettable microcapsules having hydrophobic polymer coated cores and to processes for their preparation; in particular, to microcapsules with ethylcellulose coatings that are wettable so that they are suspendible in aqueous medium. The microcapsules produced by this invention are suitable to be manufactured into oral pharmaceutical dosage forms such as capsules, tablets, monodose sachets, syrups.

BACKGROUND OF THE INVENTION

Microencapsulation by phase separation is extensively used in the preparation of multiparticulate dosage forms. The process involves enveloping small particles of the material to be delivered (typically a drug), which may be a liquid or a solid, to produce minute discrete packages called microcapsules. They comprise cores coated with an external polymeric membrane. To the naked eye microcapsules appear as a fine powder. Their dimensions typically range between few microns and thousands of microns.

Phase separation processes exploit the physico-chemical properties of a polymeric coating material which allows separation of the polymeric material from solutions in a liquid state instead of precipitating the material as a solid. The material to be coated must be insoluble in the liquid vehicle used and be compatible with the coating polymer. The material to be coated, e.g. a drug, may already be coated with an insoluble coat before it is further coated by phase separation. The separation (or coacervation) phenomenon can be induced by a number of means such as by variation of temperature and/or pH, by adding a salt or non-solvent or incompatible polymers, or by polymer-polymer interaction. Microencapsulation systems are also described in U.S. Pat. No. 3,415,758 and U.S. Pat. No. 3,748,277.

The choice of both coating polymer and microencapsulation system depends on the physico-chemical characteristics of the material to be coated and the intended purpose (therapeutic use) of the microcapsules. Microcapsules having an outer coat of polymer with hydrophobic properties, such as for example, ethyl cellulose, are extensively used as, for example, sustained release or delayed release dosage forms or taste masked dosage forms etc. Such materials may also be used for the separation of incompatible drugs.

The hydrophobic nature of such coating materials gives rise to several drawbacks when the microcapsules are to be used in aqueous environment. For example, when the finished dosage form is placed into a glass of water the hydrophobic microcapsules tend to float and form aggregates (e.g. clumps or clusters) and some tend to attach to the glass wall. The floating effect also occurs for those microcapsules having a real density greater than the liquid medium. Accordingly, for dosage forms which are to be suspended there are problems of accuracy of dosing and problems of patient acceptability due to for example difficulty with swallowing.

Aggregation and water repellence also occur in physiological fluids following the intake of dosage form containing hydrophobic microcapsules. This aggregation of the microcapsules, not only decreases the dissolution profile of the active due to a lowering of the total surface area, but also can be responsible for local irritation occurring in the gastrointestinal mucosa. Such phenomena severely prejudice both patient acceptability and therapeutic efficiency of such micro-encapsulated drugs.

U.S. Pat. No. 4,259,315 attempted to solve the above-mentioned drawbacks by admixing surfactants with hydrophobic microcapsules obtained by phase-separation This system, requiring an additional mixing step is time consuming and has drawbacks with achieving uniformity of the mixture.

FR-A-2 641 188 discloses ethylcellulose microcapsules containing sodium docusate either in-bulk or deposited onto the microcapsule surface; the surface treatment, performed by mixing the microcapsules with a docusate solution, is reported to produce a lesser effect on dissolution times than the in-bulk treatment; the amount of docusate contained in the microcapsules is not specified.

There is a need therefore for microcapsules which are wettable and which preferably do not aggregate or suffer from any one or more of the drawbacks discussed above. There is also a need for microcapsules prepared using hydrophobic polymer which are readily dispersible in water.

The present invention provides wettable microcapsules comprising a drug encapsulated by ethylcellulose, and having deposited thereon one or more surfactants and optionally a binder, wherein:

(i) the quantity of dry surfactant expressed as % w/w over the hydrophobic cores ranges from 0.010% and 2.000%;

(ii) said surfactant and optional binder have been deposited by spray-coating the microcapsules, in a fluidized bed, with a solution having a concentration of surfactant+(optional) binder comprised between 0.01 and 10.0% by weight, in a solvent in which the said ethylcellulose forming the outer membrane of the microcapsule is insoluble, and drying, (iii) said ethylcellulose being applied onto said drug by phase separation.

The present invention further provides a process to prepare said wettable microcapsules comprising spray-coating a drug particle encapsulated in ethylcellulose, with a solution having a concentration of surfactant+(optional) binder comprised between 0.1 and 10.0% by weight in a solvent in which the said ethylcellulose is insoluble, and drying to form an outer layer of surfactant.

The present invention further provides wettable microcapsules obtainable by any one of the processes described herein.

The wettability of the hydrophobic membrane of the microcapsules is achieved by coating the microcapsules (optionally) treated with surfactant during coacervation step and/or washing step as described below) with a surfactant layer, and optionally a binder. The surfactant layer is applied by spray coating the microcapsules in a fluidized bed with at least one surfactant dissolved in a suitable solvent in which the ethylcellulose forming the outer membrane of the microcapsule is insoluble, and drying.

The wetting solution composition comprises at least one surfactant and optionally a binder. The solvent may be aqueous or organic. The ethylcellulose membrane should be insoluble in the wetting solution solvent. A non limiting list of suitable binders includes gelatine, polyethyleneglycol, hydroxypropylmethylcellulose, methylcellulose, polyvinylpyrrolidones, pre-gelatinised starch, ethylcellulose, alginates, carboxymethylcellulose, arabic gum, tragacanth gum etc.

The wetting solution preferably comprises sodium docusate (DOSS) as surfactant and polyvinylpyrrolidine (PVP) as binder, both dissolved in purified water as solvent. Advantageously, the weight ratio of surfactant (eg DOSS) to binder (eg. PVP) is preferably in the range of 5:1 to 1:5, more preferably from 3:1 to 1:3. The wetting solution concentration (% w/w) of surfactant and binder (eg. DOSS+PVP) may vary from 0.1 to 10.0, advantageously from 2.0 to 6.0

To ensure the water wettability of the ethylcellulose microcapsules, the quantity of dry surfactant (eg DOSS), expressed as % w/w over the hydrophobic cores, ranges from 0.010 to 2.000, more preferably from 0.040 to 1.000.

The wettability of a solid is strictly related to its solid surface tension and that of the surrounding liquid. Solids will not be wetted if the critical surface tension is exceeded by the surface tension of the liquid. The wetting properties of a liquid medium are qualified through the determination of the contact angle (°) which is the angle between a liquid droplet and the surface over which it spreads and represents the grade of extension of a liquid on a solid surface.

The contact angle may vary from 0° signifying complete wetting, or may approach 180° at which wetting is insignificant. A primary function of the surfactants is to act as wetting agent because of their tendency to be adsorbed at the solid-liquid interfaces while reducing also the surface tension of the liquids. As a result the contact angle between the surface and the wetting liquid decreases.

The phase separation process can be carried out according to the known processes whereby the material to be located is dispersed in a solvent in which the polymeric coating is dissolved. Organic coacervation processes are particularly suitable for use in the present invention. These are widely described, e.g. in U.S. Pat. Nos. 4,315,758 and U.S. Pat. No. 3,748.277.

Preferably, the encapsulation by ethylcellulose is preferred by:
(a) forming a bisphasic system having a liquid phase comprising a ethylcellulose solution and a solid phase comprising the core to be coated;
(b) depositing the ethylcellulose on to the core in the liquid phase by phase separation;
(c) hardening the polymer coating membrane;
(d) separating the microcapsules from the liquid phase; and optionally
(e) washing the microcapsules with a liquid in which the coating membrane is substantially insoluble and separating the microcapsule from the liquid;
(f) treating the microcapsule with at least one surfactant dissolved in a liquid vehicle in which the coating polymer is substantially insoluble; and
(g) drying.

The dissolution of the coating material in the solvent may be achieved e.g., by increasing the temperature and agitating the mixture constantly. Phase separation may be (coacervation) (induced, e.g. by lowering the temperature, by adding a non-solvent or by adding a polymeric phase inducer which shows a higher affinity for the liquid vehicle (i.e. by salting out). If a phase inducer is used one or more washing phases are preferred in order to eliminate the phase inducer. The liquid vehicle may suitably be the same for phases (a), (e) and (f), or they may be different. Step (e) may be repeated. In step (e) or, if step (e) is repeated, then in either or both of steps (e), at least one surfactant may be present in the liquid used to wash the microcapsules.

The microcapsules produced according to the present invention are readily suspendible in an aqueous environment without giving rise to significant aggregation and water repellence. Furthermore the formulations prepared allow precise dosage of the drug and so allow adsorption of the drug along the gastrointestinal tract to be more homogeneous.

Solvents and complementary phase separation inducers which may be utilised in the present invention, either individually or in combination, are discussed below. These are given by way of example only and are not to be considered exhaustive.

Complementary polymer inducers include polyethylene, polybutadiene, polydimethyl-siloxane, copolymers of isobutylene and isoprene methacrylic polymers, paraffin waxes, hexane. Polyethylene and paraffin wax are preferred.

Solvents which may be used for the phase separation include methylethylketone, isobutylmethylketone, acetone, tetrahydrofuran, 1,4-dixoane, ethyl acetate, butyl acetate, cyclohexane, normal-hexane, toluene, toluene-ethanol, benzene. Cyclohexane is preferred.

Surfactants which may be used in the present invention include amphiphilic, cationic, anionic and non ionic surfactants (following the classification provided by Schwartz and Perry in "Surface Active Ingredients, Interscience, New York, 1949"). The surfactant/s selected should be soluble in the solvent in which the hydrophobic polymer is insoluble. Preferably the surfactant should have a high affinity for the hydrophobic polymer.

Particularly preferred embodiments of the invention involve the use of cyclohexane as solvent, and at least one of sodium docusate, sorbitan laurate and sorbitan oleate as surfactant.

Phase separation of ethylcellulose from cyclohexane using polyethylene or paraffin waxes are phase inducer are known methods of microencapsulation which may be used to encapsulate active principles which are insoluble in cyclohexane. Ethylcellulose/cyclohexane systems are particularly suitable because they employ a single solvent and a phase inducer. Polyethylene is a useful phase inducer as it precipitates out of the liquid medium the membrane has formed around the core.

The general procedure for the preparation of ethylcellulose microcapsules by phase separtion from cyclohexane with any phase inducer polymer is essentially as follows:
(2) disperse the ethylcellulose, the active to be coated, and the phase inducing polymer in cyclohexane at room temperature,
(2) heat the mixture, while stirring at about 78–81° C.,
(3) cool the system to room temperature to allow the ethyl cellulose coating layer to form and harden,
(4) stop agitation and decant microcapsules,
(6) filter the microcapsules and dry.

The wetting treatment is carried out once the ethylcellulose has been deposited on the core, by coating the microcapsules with at least one surfactant dissolved in a solvent in which the membrane is insoluble. Preferably surfactants which are soluble in cyclohexane are used. The post wetting treatment may conveniently be carried out at a temperature below the solubilising temperature of ethylcellulose in such solvent e.g. less than about (77–78° C.) and preferably at room temperature. The surfactant layer is applied in a separate after-step by spray coating with a solution of the surfactant and drying.

A non limiting list of surfactants which are soluble in cyclohexane at room temperature is sorbitan monolaurate (e.g Span 20), sorbitan monooleate (e.g Span 80), sorbitan trioleate (e.g Span 85), mono and diglycerides of fatty acids (e.g Arlacel 186) and sodium docusate.

Preferably the wetting treatment is carried out after the removal of the amount of cyclohexane used to dissolve ethyl cellulose and later to provide temperature-dependent gelation of the membrane. A solution of a surfactant (e.g. sodium docusate in cyclohexane) may be added to the ethylcellulose microcapsules remaining in the reactor. Agitation is required to achieve a chemical equilibrium between the two phases of the system (hydrophobic membrane/surfactant(s) solution). Agitation time required will depend on the affinity of the surfactant of the hydrophobic polymer. Once chemical equilibrium is reached further stirring will not provide any improvement in the wettability grade of the microcapsules in an aqueous medium.

The process is preferably concluded by filtering and drying the wettable microcapsules.

When a biphasic system of sodium docusate in cyclohexane and microcapsules of ethylcellulose is utilised the ratio of surfactant dissolved in the solvent and the total surface area of the microcapsules with range, e.g. from about 0.1 mg/cm$^2$ to about 10 mg/cm$^2$. However, it will be apparent to those skilled in the art that these limits may vary significantly in function of the types of surfactant, liquid vehicle and polymeric coating membrane used.

Since as the wettability grade of a solid in water is numerically quantified by the determination of the contact angle, a specific method was developed to compare the wettability behaviour of the treated microcapsules vs. the untreated ones. The decrease of the contact angle for wettable microcapsules was found to be inversely proportional to the concentration of the surfactants in the liquid vehicle used, at constant total surface area.

Direct application of the surfactant (optionally with binder) to the surface of the microcapsules by spraying over a fluidized bed provides predictable results since the quantity of surfactant applied can be pre-determined and if required accurately measured, eg by weight increase.

The following examples are used to illustrate the invention.

COMPARATIVE EXAMPLE

Cyclohexane (1000 g) at room temperature was poured into a stainless steel tank having a 2 litres capacity and equipped with a stirring means. To this was added a mixture also at room temperature of theophylline granules (200 g), ethylcellulose (7 g) and polyethylene (20 g).

While stirring, the temperature was increased up the boiling point of cyclohexane (circa 80° C.) and then the system was allowed to cool to room temperature. Once the phase separation has terminated, stirring was stopped and the microcapsules were allowed to settle. Thereafter the liquid vehicle was decanted off.

The hardened microcapsules were then washed at room temperature with 500 g of cyclohexane whilst stirring and then the liquid vehicle was removed according to the procedure described above.

The washing operation was repeated with the same amount of cyclohexane at room temperature and then the microcapsules with filtered and dried.

Example 1

800 g of dried theophylline microcapsules obtained according to the Comparative Example 1 were charged into a fluidized bed (Glatt® GCPG 1) equipped with a top spray insert and sprayed with 40 g of a wetting solution having the following composition (% w/w):
95 0 purified water
3 5 polyvinylpyrrolidone
1 5 sodium docusate Finally the surfactant-coated microcapsules were dried.

Example 2

Microcapsules of the abovementioned Examples were tested according to the procedures given below.
(1) Dissolution profiles were performed with the USP Dissolution Apparatus II Paddle according to the following method. 500 ml, pH 1.2, 100 rpm, 37 C., spectrophotometric determination. The results were the average of six replications.
2) The contact angle measurements in water were performed with a wettability tester (Lorezn & Wettre). The sample was prepared by compacting 1 g of microcapsules at 5000 kg/cm$^2$ through an hydraulic press SPE-CAC having a cavity with an internal diameter of 2 cm. The results derive from the average of 15 single determinations on both the sides of the tablet.
(3) The visual observations of the wettability behaviour of the microcapsules were performed by putting 500 mg of product into a breaker with 50 ml of water.

The results are reported in Table 1below:

TABLE I

Effect of the wetting treatment on theophylline granules microencapsulated with ethyl cellulose.

| Sample | In vitro dissolution (%) | | | | | Contact angle (%) | Visual observations |
|---|---|---|---|---|---|---|---|
| | 1h | 2h | 4h | 6h | 8h | | |
| Comparative Example | 14.3 | 28.3 | 54.9 | 78.5 | 93.3 | 79.0 ± 1.8 | Wettability absent Floating of the microcapsules |
| Example 1 | 14.7 | | 63.5 | | 100.3 | 18.6 ± 1.8 | Wettability excellent Sedimentation of the microcapsules |

What is claimed is:

1. A process to prepare a wettable microcapsule comprising a drug encapsulated by ethylcellulose, said ethylcellulose having deposited thereon one or more surfactants and optionally a binder, wherein the quantity of dry surfactant expressed as % w/w over the hydrophobic cores ranges from 0.010% and 2.000%, said process comprising the steps of:
applying ethylcellulose onto said drug by phase separation, thereby obtaining drug particles encapsulated in ethylcellulose
spray coating, in a fluidized bed, the encapsulated drug particle with a solution having a concentration of surfactant+optional binder comprised between 0.1% and 10.0% by weight in a solvent in which said ethylcellulose forming the outer membrane of the microcapsule is insoluble, and
drying to form an outer layer of surfactant.

2. A process according to claim 1 in which said drug particle encapsulated in a ethylcellulose, is prepared by:
forming an biphasic system having a liquid phase comprising a ethylcellulose solution and a solid phase comprising the core to be coated;
depositing the ethylcellulose on the core in the liquid phase by phase separation;
hardening the polymer coating membrane; and
separating the microcapsule from the liquid phase.

3. A process according to claim 2, wherein the weight ratio of surfactant to binder in the spray coating is in the range of 5:1 to 1:5.

4. A process according to claim 3, wherein the weight ratio of surfactant to binder in the spray coating is in the range of from 3:1 to 1:3.

5. A process to prepare a wettable microcapsule comprising a drug encapsulated by ethylcellulose, wherein;

(i) said ethylcellulose has deposited thereon one or more surfactants and a binder, (ii) said surfactant comprises sodium docusate, (iii) said binder comprises polyvinylpyrrolidone (iv) the quantity of dry surfactant expressed as % w/w over the hydrophobic cores ranges from 0.010% and 2.000%, said processing comprising the steps of:

applying ethylcellulose onto said drug by phase separation, thereby obtaining drug particles encapsulated in ethylcellulose spray coating, in a fluidized bed, the encapsulated drug particle with a solution having a concentration of surfactant and binder comprised between 0.1% and 10.0% by weight in a solvent in which said ethylcellulose forming the outer membrane of the microcapsule is insoluble, and drying to form an outer layer of surfactant.

6. A process according to claim 5, in which said drug particle encapsulated in ethylcellulose, is prepared by:

forming a biphasic system having a liquid phase comprising an ethylcellulose solution and a solid phase comprising the core to be coated;

depositing the ethylcellulose on the core in the liquid phase by phase separation;

hardening the polymer coating membrane; and separating the microcapsule from the liquid phase.

7. A process according to claim 6, wherein the weight ratio of surfactant to binder in the spray coating is in the range of 5:1 to 1:5.

8. A process according to claim 7, wherein the weight ratio of surfactant to binder in the spray coating is in the range of 3:1 to 1:3.

* * * * *

UNITED STATES PATENT AND TRADEMARK OFFICE
CERTIFICATE OF CORRECTION

| | | |
|---|---|---|
| PATENT NO. | : 6,509,034 B1 | |
| DATED | : January 21, 2003 | |
| INVENTOR(S) | : Massimo Maria Calanchi et al. | |

It is certified that error appears in the above-identified patent and that said Letters Patent is hereby corrected as shown below:

<u>Title page,</u>
Item [57], ABSTRACT, replace the following ABSTRACT:

-- Wettable microcapsules having hydrophobic polymer coated cores and processes for their preparation are disclosed. In particular, the present invention relates to microcapsules with hydrophobic polymer coats that are wettable so that they are suspendible in aqueous medium. The wettable microcapsules can be prepared by applying hydrophobic polymer onto a drug containing core by phase separation from a solvent to provide microcapsules, optionally washing the microcapsules with a solvent in which the microcapsules are substantially insoluble and drying, characterized in that the microcapsule is spray-coated with one or more surfactants optionally in the presence of a binder. --

<u>Column 7,</u>
Line 17, the word "processing" should be -- process --.

Signed and Sealed this

Fifth Day of August, 2003

JAMES E. ROGAN
*Director of the United States Patent and Trademark Office*